(12) United States Patent
Beerwerth et al.

(10) Patent No.: US 10,413,748 B2
(45) Date of Patent: *Sep. 17, 2019

(54) SKIN TREATMENT DEVICE

(71) Applicant: Braun GmbH, Kronberg (DE)

(72) Inventors: Frank Beerwerth, Kaltenholzhausen (DE); Christian Neyer, Eschborn (DE); Dalibor Dadic, Koenigstein (DE); Felix Heinemann, Frankfurt am Main (DE)

(73) Assignee: Braun GMBH, Kronberg (DE)

( * ) Notice: Subject to any disclaimer, the term of this patent is extended or adjusted under 35 U.S.C. 154(b) by 89 days.

This patent is subject to a terminal disclaimer.

(21) Appl. No.: 15/419,254

(22) Filed: Jan. 30, 2017

(65) Prior Publication Data

US 2017/0216619 A1   Aug. 3, 2017

(30) Foreign Application Priority Data

Feb. 2, 2016 (EP) .................................... 16153812
Jan. 19, 2017 (EP) .................................... 17152196

(51) Int. Cl.
*A61N 5/06* (2006.01)
*A61B 18/20* (2006.01)
*A61B 18/00* (2006.01)

(52) U.S. Cl.
CPC .......... *A61N 5/0616* (2013.01); *A61B 18/203* (2013.01); *A61N 5/0617* (2013.01);
(Continued)

(58) Field of Classification Search
CPC ............ A61B 18/18; A61B 2018/1807; A61B 18/203; A61B 2018/00315;
(Continued)

(56) References Cited

U.S. PATENT DOCUMENTS 6,459,919 B1 * 10/2002 Lys ...................... A61N 5/0616
                                                            315/291
6,528,954 B1 *  3/2003 Lys ...................... A61N 5/0616
                                                            315/158
(Continued)

FOREIGN PATENT DOCUMENTS

WO     WO-2006/005443     1/2006

OTHER PUBLICATIONS

European search report dated Jul. 20, 2016.
(Continued)

*Primary Examiner* — Ahmed M Farah
(74) *Attorney, Agent, or Firm* — Ronald T. Sia; Kevin C. Johnson

(57) ABSTRACT

The present invention is concerned with a skin treatment device, in particular a temporal hair removal device, having a light emission unit having a substrate, a plurality of first LED dies mounted on the substrate on an area of at least 0.2 cm$^2$, in particular of at least 1.0 cm$^2$, where the first LED dies are each arranged for emitting light at a first peak emission wavelength in the far red or infrared wavelength range of between 700 nm and 980 nm, and at least one second LED die arranged for emitting light at a second peak emission wavelength in the visible wavelength range of between 400 nm and below 700 nm, wherein the skin treatment device is arranged to activate the first LED dies to emit a treatment light pulse, the treatment light pulse in particular having a pulse length of between 10 ms and 300 ms, and the first LED dies have a radiant flux such that a radiant fluence on the skin of a user of at least 1 J/cm$^2$ is achieved by application of the treatment light pulse, and the skin treatment device is arranged to activate the at least one second LED die to emit a visible light pulse simultaneously with the emission of the treatment light pulse.

17 Claims, 6 Drawing Sheets

(52) U.S. Cl.
CPC ............ *A61B 2018/00476* (2013.01); *A61N 2005/0626* (2013.01); *A61N 2005/0644* (2013.01); *A61N 2005/0651* (2013.01); *A61N 2005/0652* (2013.01); *A61N 2005/0663* (2013.01)

(58) Field of Classification Search
CPC ........... A61B 2018/00452; A61B 2018/00476; A61N 5/06; A61N 5/0613; A61N 5/0616; A61N 5/0617; A61N 2005/0626; A61N 2005/0644; A61N 2005/065; A61N 2005/0651; A61N 2005/0652; A61N 2005/0658; A61N 2005/0659; A61N 2005/0662; A61N 2005/0663
USPC ............................... 606/3, 9–11; 607/88–92
See application file for complete search history.

(56) References Cited

U.S. PATENT DOCUMENTS

| | | | |
|---|---|---|---|
| 6,663,659 B2 | 12/2003 | McDaniel | |
| 8,961,578 B2 | 2/2015 | Liu et al. | |
| 9,375,281 B2 | 6/2016 | Moench et al. | |
| 2007/0038206 A1* | 2/2007 | Altshuler | A61B 18/203 606/20 |
| 2007/0185553 A1 | 8/2007 | Kennedy | |
| 2007/0198004 A1 | 8/2007 | Altshuler et al. | |
| 2007/0255355 A1* | 11/2007 | Altshuler | A61B 18/203 607/86 |
| 2007/0276455 A1* | 11/2007 | Fiset | A61C 19/066 607/91 |
| 2009/0018621 A1 | 1/2009 | Vogler et al. | |
| 2010/0114007 A1 | 5/2010 | Fischer et al. | |
| 2010/0145321 A1 | 6/2010 | Altshuler et al. | |
| 2011/0037844 A1* | 2/2011 | Johnson | A61N 5/0613 348/77 |
| 2012/0116373 A1 | 5/2012 | Moench et al. | |
| 2012/0226268 A1* | 9/2012 | Liu | A61B 18/203 606/9 |
| 2014/0114231 A1* | 4/2014 | Rostro | A61N 5/062 604/20 |
| 2014/0303547 A1 | 10/2014 | Loupis et al. | |
| 2016/0287333 A1* | 10/2016 | Morrison | A61B 18/203 |
| 2017/0215958 A1* | 8/2017 | Beerwerth | A61B 18/18 |
| 2017/0215959 A1* | 8/2017 | Beerwerth | A61B 18/18 |
| 2017/0216619 A1* | 8/2017 | Beerwerth | A61N 5/0616 |

OTHER PUBLICATIONS

European search report dated Feb. 28, 2017.
U.S. Appl. No. 15/419,229, filed Jan. 30, 2017, Frank Beerwerth et al.
U.S. Appl. No. 15/419,245, filed Jan. 30, 2017, Frank Beerwerth et al.
U.S. Appl. No. 15/419,214, filed Jan. 30, 2017, Frank Beerwerth et al.

* cited by examiner

SKIN TREATMENT DEVICE

FIELD OF THE INVENTION

The present invention is concerned with a skin treatment device, in particular with a temporal hair removal device, comprising a plurality of LED dies.

BACKGROUND OF THE INVENTION

It is known that skin can be treated with relatively high intensity light in order to achieve certain effects such as skin rejuvenation and in particular (temporal) hair removal (a.k.a. temporal hair growth reduction). Most known light based skin treatment devices suitable for at least temporal hair removal make use of laser light sources or flash lamps as both light sources can provide high intensity light in short pulses. LEDs have generally been described as one alternative light source.

Document US 2012/0116373 A1 discloses a light application apparatus for applying light to an object. The apparatus comprises a light source for generating processing light and sensing light, where a control unit controls the light source such that processing light in a processing time interval and sensing light in a sensing time interval are generated alternately. The light source is preferentially a solid state light source, in particular a light emitting diode or a laser diode. It is preferred that the light source comprises a VCSEL. The processing light preferentially has a wavelength in the range of 570-1200 nm and an energy density in the range of 2-30 J/cm$^2$ and a pulse duration within 1 to 600 ms.

It is an object of the present disclosure to provide a skin treatment device comprising a plurality of LED dies that is improved over the known devices or at least provides an alternative.

SUMMARY OF THE INVENTION

In accordance with one aspect there is provided a skin treatment device, in particular a temporal hair removal device, having a light emission unit having a substrate, a plurality of first LED dies mounted on the substrate on an area of at least 0.2 cm$^2$, in particular of at least 1.0 cm$^2$, where the first LED dies are each arranged for emitting light at a first peak emission wavelength in the far red or infrared wavelength range of between 700 nm and 980 nm, and at least one second LED die arranged for emitting light at a second peak emission wavelength in the visible wavelength range of between 400 nm and below 700 nm, wherein the skin treatment device is arranged to activate the first LED dies to emit a treatment light pulse, the treatment light pulse in particular having a pulse length of between 10 ms and 300 ms, and the first LED dies have a radiant flux such that a radiant fluence on the skin of a user of at least 1 J/cm$^2$ is achieved by application of the treatment light pulse, and the skin treatment device is arranged to activate the at least one second LED die to emit a visible light pulse simultaneously with the emission of the treatment light pulse.

In accordance with one aspect there is provided method of cosmetic skin treatment, in particular of cosmetic hair removal, the method comprising the steps of:
providing a substrate and a plurality of first LED dies mounted on the substrate being arranged for emitting light at a first peak emission wavelength in the far red to infrared wavelength range of between 700 nm and 980 nm;
providing a second LED die being arranged for emitting light in the visible wavelength range of between 400 nm and below 700 nm;
activating the first LED dies to emit a treatment light pulse; and
activating the at least one second LED die to emit a visible light pulse simultaneously with the treatment light pulse.

BRIEF DESCRIPTION OF THE DRAWINGS

The present disclosure will be further elucidated by a description of example embodiments in which description reference is made to figures. In the figures

DETAILED DESCRIPTION OF THE INVENTION

Figure 1:
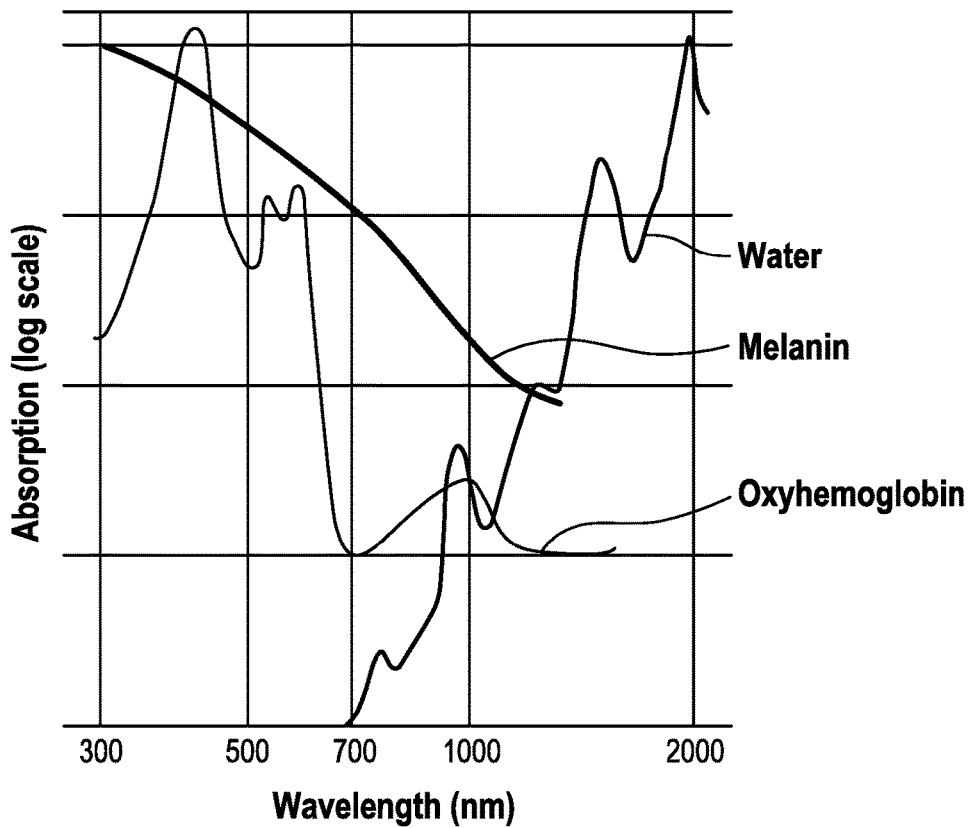
FIG. 1 is a graph showing the absorption coefficient for melanin, water, and oxyhemoglobin on a logarithmic scale vs. the wavelength of light between 300 nm and 2000 nm.

It is generally known that various types of skin treatment can be affected by applying light (in particular in the form of at least one treatment light pulse) to the skin. Such skin treatments encompass skin rejuvenation, wrinkle reduction, acne treatment, and (temporal and permanent) hair removal (also named hair growth reduction or hair growth management, as hairs are not necessarily immediately removed by the application of light). The skin treatments can be grouped into cosmetic treatments such as hair removal for mere cosmetic reasons and non-cosmetic (e.g. prophylactic therapeutic) treatments. In particular, skin treatment for achieving temporal and/or permanent hair removal (hair growth reduction—in the following just "hair removal" is used) requires a radiant flux emitted by the LED die array per unit area that is much higher than the radiant flux that is required for skin rejuvenation or the like. For the application of treatment light pulses onto the skin various light sources have been discussed such as laser light sources, flash lamps (e.g. Xenon arc lamps), and semiconductor light sources such as LEDs. While laser light sources and flash lamps have been widely discussed with respect to hair removal, the application of LEDs as light source has been discussed in much less detail, in particular as the required radiant fluence to be applied on the skin within a short pulse length (e.g. below 10 ms) are easily delivered by lasers or flash lamps. Now, the present disclosure is directed to semiconductor light sources (where in the following the term LED is used, this shall encompass other solid state light sources such as VCSELs, VECSELs, or OLEDs), in particular arrays of LED dies (i.e. semiconductor dies in contrast to packaged LEDs), and their use for light-based temporal or permanent hair removal.

LED dies can emit light at essentially any wavelength from ultraviolet (UV) light to infrared (IR) light, i.e. from about 280 nm to 1300 nm, e.g. depending on the used semiconductor material. LED dies emit light with a relatively narrow spectral bandwidth of $\Delta\lambda \cong \pm\lambda/20$. Where in the present disclosure the term "wavelength" is used in relation to an LED die, this wavelength means the peak emission wavelength, i.e. the wavelength at the maximum of the light emission curve of the LED die.

In accordance with the present description the plurality of first LED dies emit light at a peak emission wavelength in the far red to infrared wavelength range of between 700 nm and 980 nm, in particular in a range of between 700 nm and 880 nm. In some embodiments, the first LED dies emit light at a peak emission wavelength in the range of between 700 nm and 760 nm or in the range of between 820 nm and 880 nm. In some embodiments, a first sub-plurality of first LED dies emit light at a peak emission wavelength in the range of between 700 nm and 760 nm and a second sub-plurality of first LED dies emit light at a peak emission wavelength in the range of between 820 nm and 880 nm. In In accordance with the present description, at least one second LED die emits light at a peak emission wavelength in the visible light wavelength range, i.e. in the range of between 400 nm and 700 nm in order to enable emission of a visible light pulse simultaneously with the emission of a treatment light pulse by the first LEDs. As the treatment light pulse in the far red to infrared wavelength range is essentially invisible to the human eye, the simultaneous visible light pulse allows a user to better understand when a treatment light pulse is emitted. In particular if the visible light pulse is as long as the treatment light pulse, the user then understands that the device is to be kept on the skin. It is also a visible confirmation that an invisible treatment light pulse is generated by the device. As will be explained in more detail, the at least one second LED die can also be used to emit visible light not during the treatment pulse, e.g. for mere illumination purposes to help a user placing the skin treatment device or in order to identify a selected active area of first LED dies.

In some embodiments, the at least one second LED die is also mounted on the substrate. But this does not need to be the case and the second LED die can be placed elsewhere. In some embodiments, the visible light pulse and the essentially invisible treatment light pulse are directed through a common exit window of the device. In some embodiments, at least two second LED dies are provided, where the two second LED dies emit at different peak emission wavelengths in the visible wavelength range. In some embodiments, at least three second LED dies are provided that each emit at a different peak emission wavelength in the visible range so that a neutral white color pulse can be generated. In some embodiments, the skin treatment device is arranged to control at least the intensity (only a single second LED die is needed) or a color (at least two second LED dies emitting at different peak emission wavelengths in the visible wavelength range are needed) of the visible pulse in dependence on at least one of a user's input, a chosen skin treatment function, a radiant fluence applied by the treatment light pulse, a battery charge status, or a device temperature value. The second LED die(s) can then be used to also communicate further information, e.g. that the skin treatment device's battery or batteries should be recharged or replaced. In some embodiments, the skin treatment device comprises a switch for user-controlled activation of a visible light pulse from the at least one second LED. The user may use such a function to illuminate the skin that is to be treated prior to placing the device on the skin.

In some embodiments, the skin treatment device can be switched between a hair removal function and another skin treatment function such as a skin rejuvenation function or an acne treatment function or a wrinkle reduction function.

In some embodiments, the skin treatment device has a control unit that is connected with the plurality of LED dies for selectively activating the LED dies. The control unit may activate the first LED dies to emit a treatment light pulse and simultaneously the second LED dies is activated. The control unit may be arranged for (a) selectively switching on or off the at least one second LED die outside of a treatment light pulse (e.g. as a response to a user input triggering a visible light pulse for illumination purposes), or (b) switching on or off individual LED dies during the treatment light pulse or at least during a portion of the treatment pulse, or (c) controlling the forward current of at least one LED die during the treatment light pulse.

In one aspect, the following description is focuses on skin treatment devices having a light emission unit with a plurality of substrate mounted first LED dies (which may be mounted in the form of a regular array pattern, but the first LED dies may also be mounted in an irregular manner) that are able to deliver a radiant fluence in a range of between 1 J/cm$^2$ to 8 J/cm$^2$ (in particular of 1 J/cm$^2$ to 7 J/cm$^2$) by applying light pulses in a range of between 10 ms and 300 ms, in particular in a range of between 20 ms and 200 ms, and further in particular of a range of between 30 ms and 200 ms or 30 ms and 100 ms. In the present disclosure, use is made of relatively long treatment light pulses. It is known that the coagulation needed for bringing a hair follicle into apoptosis (programmed cell death) is a function of both, temperature and time. Hence, while a temperature exposure of 70 degrees Celsius over 1 ms leads to coagulation of proteins in a hair follicle, a temperature of 62 degrees Celsius leads as well to the needed coagulation if the hair follicle is exposed to this temperature over a period of 100 ms. Thus, while a pulse length of 10 ms and higher is contemplated, a radiant fluence in the range of 4 J/cm$^2$ and higher, which is in particular used to treat brown hair on pale skin, requires that treatment light pulses having a pulse length of at least 60 ms, further in particular of at least 100 ms are used in at least one or several treatment modes. This is in particular the case when different LED dies arranged for emitting at different wavelengths are mounted on the substrate. Thus, in accordance with at least one aspect, the skin treatment device is arranged to emit at least one treatment light pulse having a pulse length of at least 60 ms, in particular pulse lengths in a range of between 80 ms and 120 ms, typically around 100 ms.

At least some of the LED dies mounted on the substrate have a mounting density and light output power (radiant flux) that is sufficient to affect at least temporal hair removal. This will be explained more in detail in following paragraphs.

In one aspect, the following description focuses on skin treatment devices that comprise a light emission unit with substrate mounted first LED dies arranged for emitting at a first wavelength in the invisible wavelength range and at least one second LED die arranged for emitting at a second wavelength in the visible wavelength range. In some embodiments, the first LED dies have a mounting density and light output power (radiant flux) sufficient for affecting at least temporal hair removal. In some embodiments, the second LED die may be arranged to emit the visible light at a lower radiant flux sufficient for illumination purposes. As different LED dies can easily be mounted on the same substrate, first LED dies arranged for treatment and second LED dies arranged for illumination can be arranged on the same mounting area and can be separately controlled by respective individual wiring. In some embodiments, LED dies of the same kind are controlled as a group instead of being individually controlled. In particular, LED dies can be arranged in series and can then be controlled as a group. LED dies of a single row or column of an array of LED dies may thus be connected in series, but of course the position of the LED dies that should be controlled at the same time is arbitrary.

For sake of completeness, where the present disclosure uses the term "pulse length", this time period means the pulse length measured at full-width-half-maximum (FWHM) pulse intensity.

While the "radiant fluence" is here provided as a value on the skin of the user, it is to be understood that the skin treatment device as described herein either has the LED dies located essentially at the level of an exit opening or the substrate area mounted with LED dies is surrounded by a casing having reflective inner walls, so that the radiant fluence on the skin of the user (during regular operation) means the radiant fluence that is emitted at the location of the LED dies because the substrate area to which the LED dies are mounted is of the same size as the area of the skin treated. In cases, where the light emitted by the LED dies is applied on the skin with a diverging beam that is not spatially limited by a reflective casing, the respective reduction factor needs to be taken into account (i.e. the radiant fluence at the LED dies level must be respectively higher than the herein defined radiant fluence on the skin).

In contrast to a flash lamp, an LED die emits in a relatively narrow wavelength band (e.g. with a spectral bandwidth (FWHM) of $\Delta\lambda \cong \pm\lambda/20$). Thus, similarly to a laser, LED dies can be chosen such that the light emitted is optimal for the particular situation (e.g. determined by hair color and/or skin color). Hence there is no need for optical filters that are typically used in IPL (Intense Pulsed Light) devices using a flash lamp, where the flash lamp emits in a very broad wavelength spectrum including UV portions that are to be filtered out for known health reasons.

In one aspect of the present disclosure, a skin treatment device comprises different first LED dies arranged for emitting treatment light at different wavelengths in the far red to infrared wavelength range, e.g. at two different wavelengths, three different wavelength etc. LED dies emitting at different wavelengths can be used to optimally tune the wavelength content to a particular situation (e.g. changing hair color and/or skin color from user to user or even for a single user, where in particular skin color depends on the tanning of the treatment area). These possibilities will be explained in more detail below.

In essence, light based hair removal aims to reduce or inhibit hair growth by thermally affecting the hair follicle without affecting the surrounding skin. In order to thermally affect the hair follicle, light must be absorbed by a target chromophore in the hair follicle. Generally, the target chromophore is melanin (i.e. typically the brownish/blackish eumelanin, but also the reddish pheomelanin, which is mostly present in red hair). FIG. 1 shows the relative light absorption of melanin, oxyhemoglobin (blood), and water on a logarithmic scale in a range of between 300 nm and 2000 nm (the absorption curves of FIG. 1 are taken from: Christine C. Dierickx, M.D. "*Laser Hair Removal: Scientific Principle and Practical Aspects*", Lumenis, 2002—www.lumenis.com). Heat generated in the melanin carrying portions of the hair follicle dissipates into the surrounding tissue and eventually leads to coagulation of proteins if the heating time and the temperature together are above a certain threshold, where—as had been explained—the temperature leading to coagulation is lower if the heating time is longer.

Figure 2:
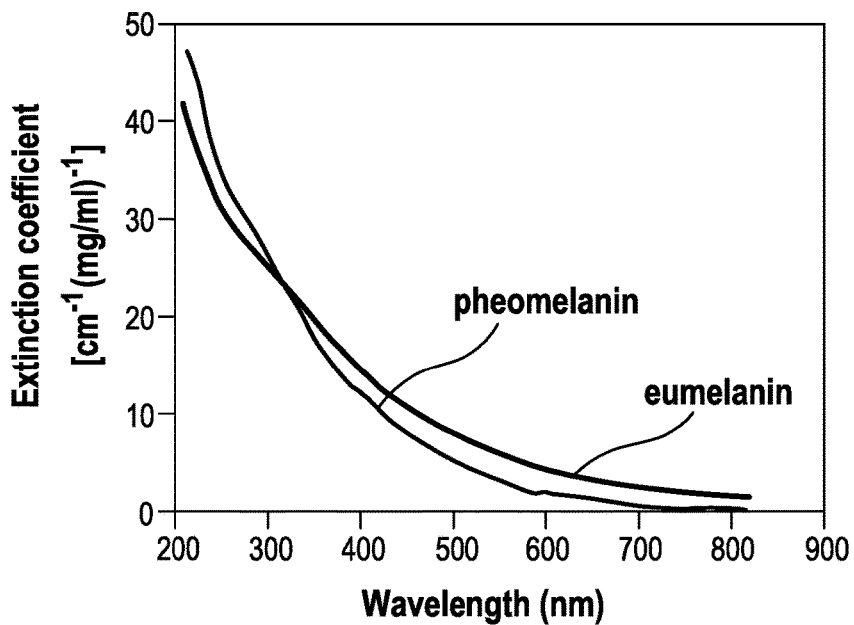
FIG. 2 is a graph showing the extinction coefficient of eumelanin and pheomelanin vs. the wavelength of light between 200 nm and 900 nm.

The present disclosure is essentially directed to a large area skin treatment device (e.g. a treatment area of at least $0.2$ cm$^2$, in particular of around 1 to 4 cm$^2$, and potentially up to about 10 cm$^2$ and to unmonitored home use (i.e. allowing a user to perform the treatment at home without the risk of injuring and without the need of professional support by medically trained personnel). Such a skin treatment device illuminates large skin areas without particularly addressing individual hair follicles. That means that skin tissue without hair follicles is as well irradiated by the treatment light pulse as well as blood vessels being present in the dermal tissue. In order to leave skin tissue and blood vessels thermally unaffected (i.e. to keep the thermal effect on skin tissue and vessels at a level acceptable for home use) in such large area treatment, optimal hair follicle treatment occurs in wavelength ranges in which the melanin absorption is high over the absorption in water and by oxyhemoglobin. Thus, for brownish/blackish hair that carries eumelanin (including blonde hair, i.e. fair brownish hair), the optimal wavelength range is between 630 nm and 900 nm, where the absorption by water and oxyhemoglobin is low in comparison to melanin. Hair removal by light application becomes difficult if eumelanin is essentially missing as chromophore and only pheomelanin can be targeted (i.e. in case of red hair), as the absorption curve for pheomelanin lies below the curve for eumelanin. FIG. 2 show the (mass) extinction coefficient curves for eumelanin and pheomelanin (taken from: T. Sarna, H. M. Swartz, *The physical properties of melanins*, in "The Pigmentary System", ed. J. J. Nordlund et al., Oxford University Press, 1988). The extinction coefficient is a parameter that defines how strongly a substance absorbs light of a certain wavelength. FIG. 2 shows that a treatment light pulse of a certain radiant fluence in the wavelength range of between 630 nm to 900 nm has less an effect on red hair and thus cannot generate a temperature in the hair follicles that is sufficiently high to cause protein coagulation. It is thus believed that red hair is best treated by applying light at a wavelength of around 500 nm (e.g. in a wavelength range of between 480 nm and 510 nm), where oxyhemoglobin has a local absorption minimum (see FIG. 1).

A major factor in setting the right parameters for light based hair removal is the understanding of the absorption of light by the melanin in the skin and the thermal burden on the skin depending on the melanin content of the skin. Melanin content of the skin, i.e. skin color, is generally related to the Fitzpatrick skin type (FST) classification scale, by which FST type I (pale white) to FST type VI (deepest pigmentation) skin types are determined. The more intense the skin color, the higher is the melanin content in the skin and the higher is the light absorption by the melanin particles in the skin and thus the higher is the thermal burden on the skin. Melanin particles in the skin have a typical size in the range of 1 μm to 5 μm, whereas hair follicles have a size in the range of 100 μm to 300 μm. The substantial difference in the size of the melanin carriers (melanin carrying portion of the hair follicles vs. melanin granules in the skin) leads to a different heat dissipation behavior. While the mentioned melanin granules in the skin have a thermal relaxation time of below 0.1 ms, hair follicles have a thermal relaxation time of around 10 ms. Now, it is generally believed that a certain radiant fluence (light energy per unit area) needs to be applied within a certain time frame in order to thermally affect hair follicles. It is believed that the pulse length shall have a value that is above the thermal relaxation time of the melanin granules in the skin in order to allow heat to dissipate from these melanin particles and to reduce the thermal burden on the skin due to light absorption by the pigments. The pulse length may thus in particular be ten times higher than the thermal relaxation time (i.e. at least about 1 ms or above). For pale to medium skin color (FST I-III) the effect of the light absorption of melanin in the skin leads to limited thermal influence and does not play a major role in the determination of optimal pulse length. Anyhow, such short light pulses of 1 ms or even below of a sufficient fluence cannot be generated by today's LED dies even if mounted with a high density as described herein. In accordance with the present disclosure, a pulse length of at least about 10 ms is considered. If the necessary radiant fluence is provided in a too long treatment light pulse, heat dissipation reduces the temperature that can be achieved in a hair follicle to a value too low for effective generation of coagulation seeds in the hair follicle. It is believed that the pulse length should not be longer than about 300 ms, in particular not longer than about 200 ms, which value is essentially determined by the thermal relaxation time of the hair follicles, and should typically be in a range of 3 to 10 times the thermal relaxation time (which may be in a range of about 10 ms, but can be higher for large hair follicles). The radiant fluence delivered during this time period shall be in the range of between 1 J/cm$^2$ to 8 J/cm$^2$ in order to achieve an effect relevant for at least temporal hair removal (i.e. a thermally affected change in at least the hair follicle so that a temporal or permanent hair growth reduction occurs). For eumelanin carrying hair and a light skin color, typically 4 J/cm$^2$ to 8 J/cm$^2$ are to be applied. The pulse length may generally be within a range of 10 ms and 300 ms, in particular 20 ms to 200 ms. As mentioned, the skin treatment device may be arranged to emit a treatment light pulse with a pulse length in the range of between 80 ms and 120 ms.

Another factor that is to be taken into account is the penetration depth of the light into the skin. The optical penetration depth (distance where the intensity of the light is reduced to 1/e) seems to vary in literature. E.g. for fair Caucasian skin penetration depth values of 0.230 mm at a wavelength of 500 nm to about 1.6 mm at a wavelength of 1000 nm are provided in one reference (R. Rox Anderson et al., The Optics of Human Skin, The Journal of Investigative Dermatology, 77: 13-19, 1981), while values of about 0.9 mm for 500 nm and 2.6 mm at 1000 nm are provided by another reference (Bashkatov, et. al.; Optical properties of human skin, subcutaneous and mucous tissues in the wavelength range from 400 to 2000 nm; J. Phys. D: Appl. Phys. 38 (2005) 2543-2555). Independent from these differences, the penetration depth generally decreases considerably from a wavelength of 1000 nm to a wavelength of 500 nm. Hair follicles are located at around 1-3 mm below the skin surface. Thus, those wavelengths believed optimal for red hair treatment have a particularly low penetration depth. The low penetration depth of low wavelength light also excludes using light of even lower wavelength, e.g. UV light of around 300 nm, which essentially would not even reach the hair follicles, besides other risks involved with UV light. Because of the strong absorption of light around 500 nm in the skin tissue, it is believed that a radiant fluence in a range of between 3 J/cm$^2$ to about 6 J/cm$^2$, in particular in a range of between 3 J/cm$^2$ to 5 J/cm$^2$, is to be applied.

As has been mentioned before, a light emission unit in accordance with the present disclosure has a substrate on which a plurality of first LED dies each having a certain radiant flux per first LED die is mounted at a sufficiently high density (e.g. between about eight to about 90 LED dies per square centimeter, but the achievable density expressed in number of dies per unit area naturally also depends on the size of the LED dies). Some examples of first LED dies suitable in accordance with the disclosure are discussed in the following.

In a first example, a plurality of first LED dies is mounted on a substrate, where each LED die of the plurality is arranged to emit in a wavelength range of between 700 nm and 780 nm. One example of an LED die emitting in this range is the LED die used in the OSLON SSL® 150 (GF CSHPM1.24—datasheet Version 1.0) from Osram GmbH, Munich, Germany. The respective LED die emits light at a peak emission wavelength of 730 nm (far red) with a spectral bandwidth (FWHM) of Δλ=±30 nm. This LED die has a radiant flux (also called radiant power) of between 201 mW and 280 mW (typical 231 mW) at a forward current of 350 mA, where a forward current of up to 1000 mA is specified (leading then to a typical radiant flux of 660 mW).

These LED dies from Osram (having a die size of about 1 mm×1 mm=1 mm$^2$) may be mounted on a substrate with a distance of about 0.2 mm so that 8 times 8=64 LED dies can be mounted on a 1 cm times 1 cm=1 cm$^2$ substrate area.

Generally, large size LED dies may have a size in the range of between 0.5 mm to 1.5 mm times 0.5 mm to 1.5 mm (i.e. a size of 0.25 mm$^2$ to 2.25 mm$^2$). LED dies may be connected to the substrate by wire bonding (in particular gold wire bonding), but in order to achieve a high packaging form factor and enhanced heat dissipation, LED dies may also be connected to the substrate via flip chip technology (a density of 89 1×1 mm$^2$ LED dies per square centimeter may thus be achieved). Driving the above mentioned Osram LED dies (density of 64 LED dies per square centimeter) at the specified forward current of 1000 mA to emit a treatment light pulse having a pulse length of between 30 ms to 200 ms leads to a radiant fluence on the skin (assuming that all radiant energy is applied onto a skin area of the same treatment area size as the mounted substrate area size) in a range of between 1.267 J/cm$^2$ and 8.448 J/cm$^2$. Access heat generated by the LED dies while emitting light pulses can be dissipated away from the substrate by a passive or active cooling arrangement, e.g. a heat sink, heat pipe, or an active liquid cooling system. Passive cooling arrangements (e.g. heat sinks) may be supported by providing an (cooled) air stream). The efficiency of LED dies often is around 30%, so that a treatment light pulse generating a radiant fluence of 8

J/cm² means that about 18.7 J/cm² of excess heat must be dissipated. In contrast to flash lamps that require a certain cooling down time of about 1 s and more, LED dies can be pulsed at a higher frequency and thus a faster overall treatment time of a large skin area can be achieved with LED dies.

In the above described first example, four LED dies from the eight times eight LED die array may be replaced by different LED dies emitting at a second wavelength different to the first wavelength (e.g. the second wavelength could lie in the visible range of between 400 nm and 700 nm so that these different LED dies then can form second LED dies) and the fluence on the skin would than still essentially cover a range of between 1 J/cm² and 8 J/cm² for a pulse length of between 30 ms and 200 ms.

In a second example, the first LED dies may be taken from the OSLON Black Series (850 nm) from Osram GmbH, Munich, Germany. In accordance with the data sheet (Version 1.1 from 2014-01-09), the respective LED die (size 1×1 mm²) emits light at a peak emission wavelength of 860 nm (centroid wavelength: 850 nm) with a spectral bandwidth (FWHM) of $\Delta\lambda=\pm30$ nm. The total radiant flux is given as 1030 mW at a forward current of 1000 mA. Already five such LED dies mounted on a substrate area of 1 cm² lead to a radiant fluence of about 1 J/cm² per 200 ms pulse length on a skin treatment area of 1 cm² (assuming that the total radiant flux of the LED die is applied onto the skin treatment area).

In a third example, again an array of 8×8 LED dies is mounted on a substrate area of 1 cm². A first sub-plurality of 44 first LED dies (OSLON SSL® 150 emitting at a first wavelength of 730 nm) is essentially mixed with a second sub-plurality of 20 first LED dies (OSLON Black Series emitting at a second wavelength of 850 nm). If only the first sub-plurality of first LED dies is switched on to emit a treatment light pulse of 200 ms, a fluence of 5.8 J/cm² can be achieved. If only the second sub-plurality of first LED dies (850 nm) is switched on to emit a treatment light pulse of 200 ms, a fluence of above 4 J/cm² can be achieved. Switched on together, a fluence of almost 10 J/cm² can be achieved in a 200 ms treatment light pulse (or a fluence of almost 5 J/cm² in a 100 ms treatment light pulse). Thirty-three 850 nm LED dies can provide a fluence of about 1 J/cm² in a 30 ms pulse.

In addition, the hair removal device may comprise Golden DRAGON Plus LV W5AM LED dies from Osram GmbH, Munich, Germany, which emit light at a peak emission wavelength of 502 nm (typical dominant wavelength of 505 nm). In accordance with the datasheet (version 1.1), the LED die has a luminous flux of 67 lm at a forward current of 350 mA. 67 lm convert to a radiant flux of about 240 mW for a wavelength of 505 nm (about 684 mW at 1000 mA forward current when a linear extrapolation is used). As the 505 nm dominant wavelength LED die emits in a spectral band around the dominant wavelength and as the lumen to Watt conversion is strongly depending on the wavelength, this value is just an estimate. Around twenty-one such 505 nm LED dies are needed per square centimeter to achieve a radiant fluence of about 3 J/cm² in a 200 ms treatment light pulse. Hence, about forty-four 505 nm LED dies per square centimeter provide the radiant fluence of 3 J/cm² in a 100 ms pulse and about eighty-eight 505 nm LEDs provide a radiant fluence about 6 J/cm² in a 100 ms pulse. About eighty-eight 505 nm LED dies can provide a radiant fluence of about 3 J/cm² in a 50 ms pulse. The hair removal device may additionally comprise a plurality of such LED dies in order to additionally provide red hair treatment capability.

It is to be understood that the values discussed here are relatively rough reference values, as the radiant flux of an LED die depends on the temperature of the LED die, the forward current and other factors.

Table 1 is a summary of wavelength, pulse length and fluence values that the inventors of the present description believe to represent optimal treatment parameters for the given hair color and FST skin type. The wavelength is understood to be a representation of a wavelength range in each case, which range should cover ±50 nm (optionally ±30 nm) around the given single wavelength value. It is noted that in some embodiments the skin treatment device comprises a first sub-plurality of first LED dies arranged for emitting light with a peak emission wavelength around 730 nm and a second sub-plurality of first LED dies arranged for emitting light with a peak emission wavelength around 850 nm so that a control unit can activate the first LED dies in accordance with Table 1 (excluding the red hair situations). Additionally, a third sub-plurality of first LED dies arranged for emitting light with a peak emission wavelength around 500 nm may be present, so that the control unit can activate the first LED dies in accordance with Table 1.

TABLE 1

Wavelength, fluence and pulse length values provided as a function of hair color and FST skin type. It is to be understood that the wavelength shall represent a range of wavelengths of ±50 nm around the given single wavelength value.

| Hair color | Skin Type [FST] | Wavelength [nm] | Pulse length [ms] | Fluence [J/cm²] |
|---|---|---|---|---|
| Light brown/ medium | I-II | 730 | 20-200 | 4-7 |
| Dark brown | I-II | 730 | 20-200 | 2-5 |
| Red | I-II | 500 | 30-200 | 3-5 |
| Light brown/ medium | III-IV | 730 + 850 | 20-200 | 4-7 |
| Dark brown | III-IV | 730 + 850 | 20-200 | 2-5 |
| Red | III-IV | 500 | 100-200 | 3-5 |
| Light brown/ medium | V-VI | 850 | 30-200 | 4-7 |
| Dark brown | V-VI | 850 | 30-200 | 2-5 |
| Red | V-VI | — | — | — |
| White/grey | All | — | — | — |

Figure 3:
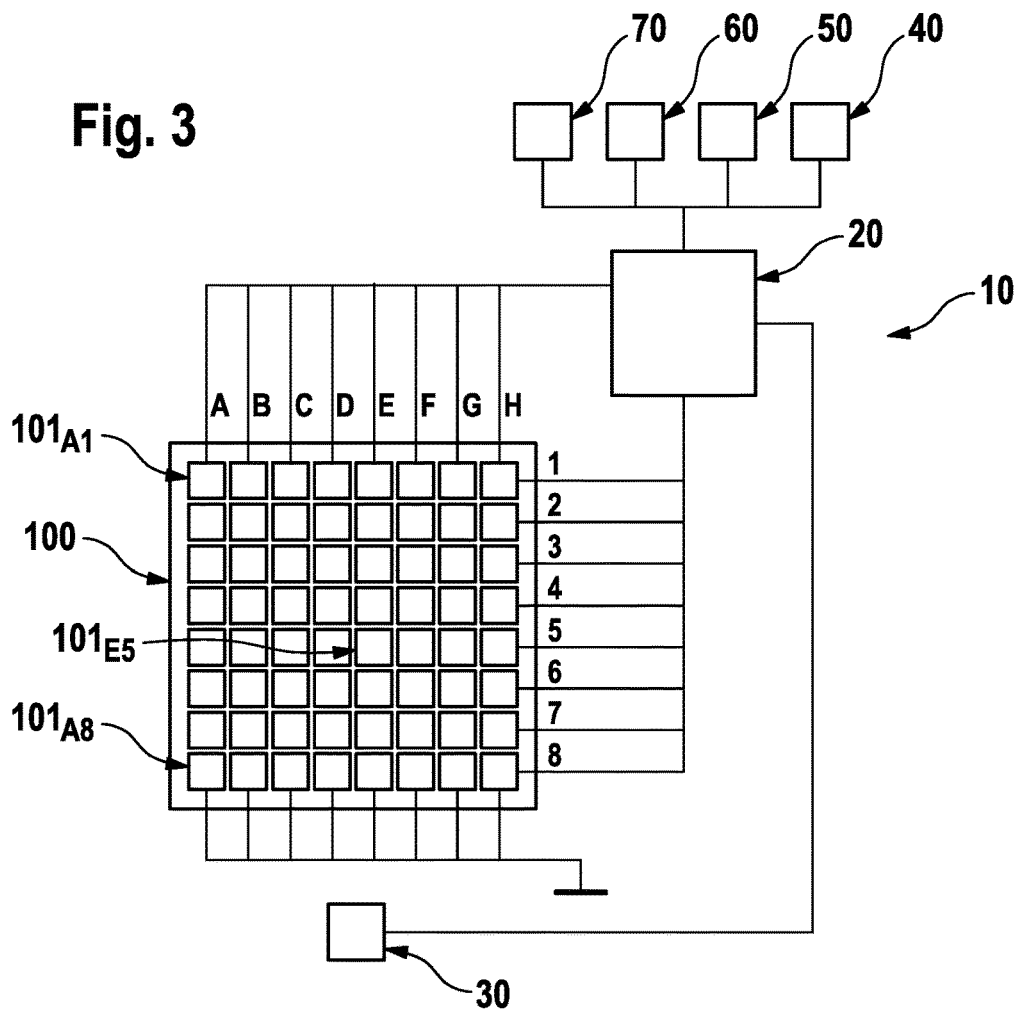
FIG. 3 is a schematic depiction of an example embodiment of a light emission unit in accordance with the present disclosure, which comprises a substrate on which an eight times eight matrix of LED dies is mounted.

FIG. 3 is a schematic depiction of an example embodiment of a light emission unit 10 in accordance with the invention. The light emission unit 10 comprises a substrate 100 on which a plurality of 64 LED dies are mounted. The LED dies are arranged in a regular rectangular 8 times 8 pattern in columns A to H and rows 1 to 8, so that the LED dies can be identified by their position in the column-row matrix. Three LED dies $101_{A1}$, $101_{A8}$, and $101_{E5}$ are exemplary identified and it shall be understood that LED dies in a matrix arrangement can be identified by their column and row added as a suffix to the respective reference numeral.

Figure 4A:
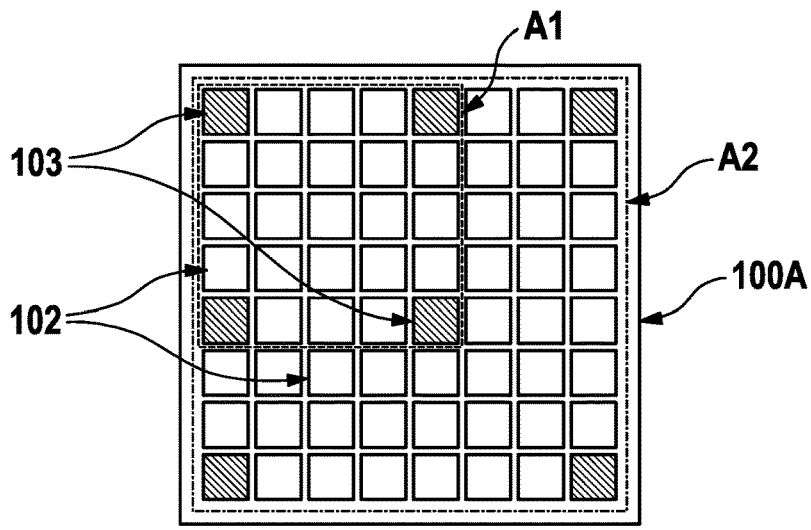
FIG. 4A is another example embodiment of an eight times eight matrix of LED dies mounted on a substrate comprising first and second LED dies.
Figure 4B:
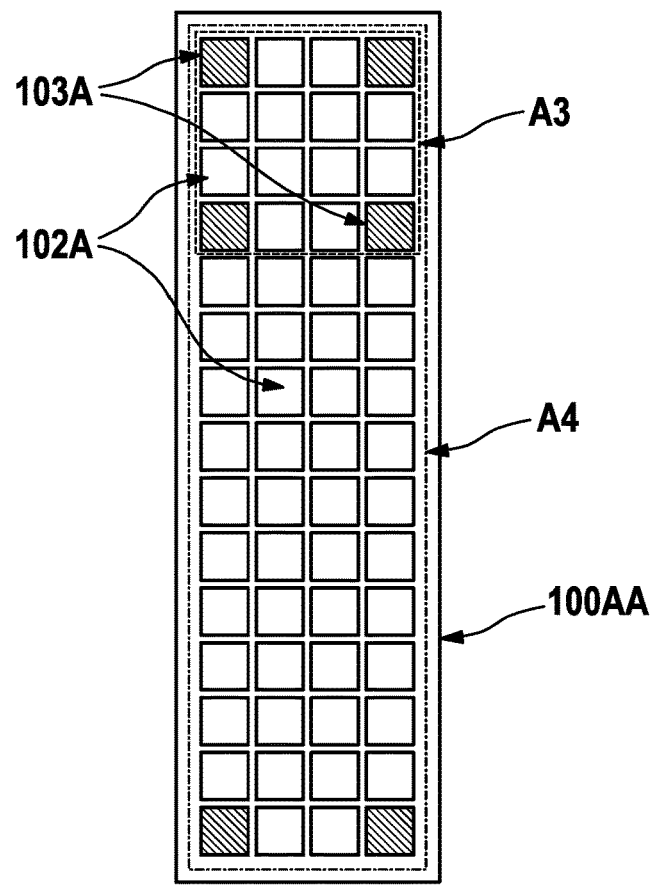
FIG. 4B is a further example embodiment of a fifteen times four matrix of LED dies mounted on a substrate comprising first and second LED dies.
Figure 5:
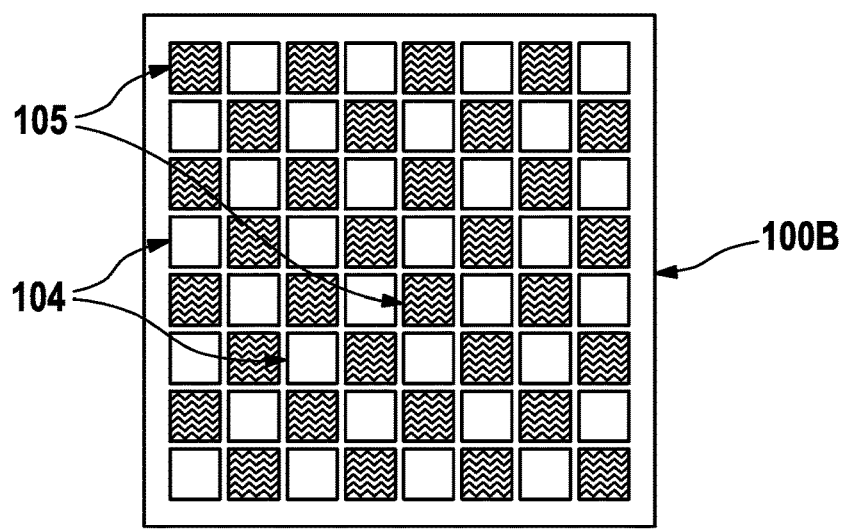
FIG. 5 is another example embodiment of an eight times eight matrix of LED dies mounted on a substrate comprising first and second LED dies.
Figure 6:
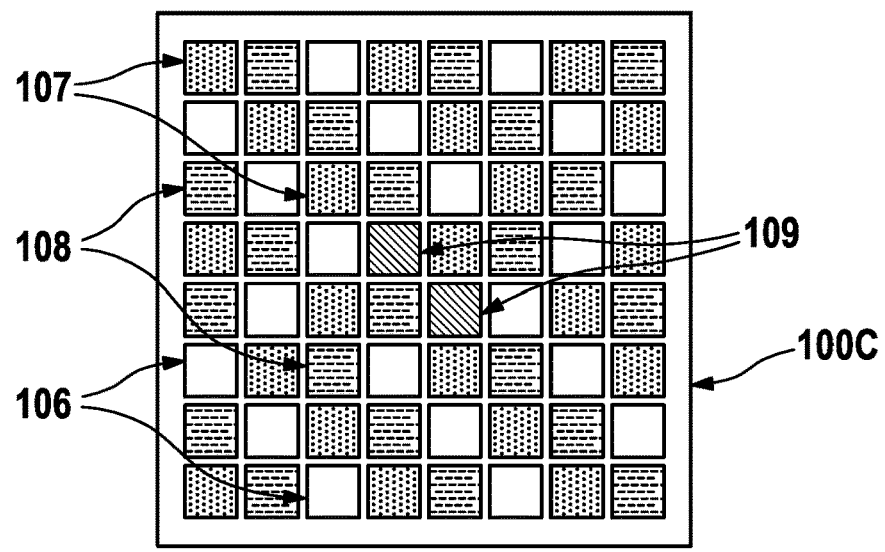
FIG. 6 is a further example embodiment of an eight times eight matrix of LED dies mounted on a substrate comprising different sub-pluralities of first LED dies and second LED dies.

It is to be understood that the shown 8 times 8 square LED die matrix is just an example and the LED dies may be arranged on the substrate in any sensible manner, either as a regular square or rectangular matrix such as a 2 times 2, a 2 times 4, a 3 times 6, a 5 times 5, a 10 times 14, a 4 times 15 (see FIG. 4B) etc. matrix or in a less structured, more random pattern. Instead of being arranged in a regular square or rectangular matrix, the LED dies may be arranged in a regular pattern, which resembles a circular region rather than a square or rectangular region. Any other shape of the mounted substrate area may be chosen as well (e.g. triangular, trapezoidal, arbitrary). In the examples of FIGS. 4A, 5 and 6, the same 8 times 8 matrix will be used for sake of simplification of the discussion, but the concepts and ideas described with respect to these figures are of course also applicable to the just mentioned other regular or irregular patterns of substrate mounted LED dies. FIG. 4B shows an embodiment with a 4 times 15 matrix.

A control unit 20 has leads connected with the matrix of LED dies in order to selectively provide voltage and current supply to each of the LED dies 101. As mentioned before, the 8 times 8 matrix has 8 columns of LED dies that are connected in series so that each of the columns is controlled at the same instant. Generally, while the control unit 20 may be arranged to simultaneously switch on and off all LED dies, the control unit 20 may also be arranged to individually switch on or off each of the LED dies mounted on the substrate. Generally, a control unit may be connected with the plurality LED dies in any suitable manner One of the LED dies 101 shown in FIG. 3 may be a second LED die, while the other 63 LED dies are first LED dies. But the second LD die may also be physically separate from the substrate on which the first LED dies are mounted.

Control unit 20 is coupled with a sensor 30 for measuring a skin property, e.g. the skin color (pigmentation level). The sensor may comprise a light source that is illuminating the skin and the sensor may be arranged to determine the skin property such as skin color from the amount of light that is backscattered to the sensor (e.g. realized by a photo diode). The control unit 20 may then in particular be arranged to control at least one treatment parameter based on the measured skin color, e.g. light intensity and/or pulse length. The sensor 30 is to be understood as an optional feature.

The control unit 20 is here also coupled with a user interface 40, 50, 60, 70 allowing the user to control aspects of the light emission unit 10. The user interface here comprises four input elements 40, 50, 60, and 70. A first input element 40 may be arranged as an ON/OFF switch. A second input element 50 may be arranged as a switch to choose a treatment type, e.g. the second input element 50 may allow a user to switch between a hair removal function and a skin rejuvenation function. The control unit 20 may then be arranged to control at least one treatment parameter based on the chosen type of treatment, e.g. the radiant flux emitted by the LED dies may be lower for a skin rejuvenation function than for a hair removal function. A third input element 60 may be arranged to allow the user to input the hair color. The control unit 20 may then be arranged to control at least one treatment parameter in dependence on the hair color. A fourth input element 70 may be arranged to allow the user to set a maximum radiant fluence value to be applied onto the skin (e.g. a value in the range of between 1 J/cm$^2$ and 8 J/cm$^2$). The control unit 20 may then be arranged to apply only light pulses with a radiant fluence not higher than the chosen maximum radiant fluence. Additionally or alternatively, one of the input elements may be arranged to allow a user or trigger a visible light pulse also outside of the duration of the treatment light pulse. The control unit 20 may then be arranged to activate the at least one second LED die to emit a visible light pulse, e.g. for illumination of the skin to be treated. Additionally or alternatively, one of the input elements may be arranged to allow the user to switch from a first active area of the mounted first LED dies to second active area (see description with reference to FIGS. 4A and 4B below). Each of the input elements 40, 50, 60, or 70 may be arranged as an input knob or a slider or as a touch sensitive switch on a touch sensitive board. In contrast of being wire-connected with the control unit 20, the user interface may be realized on a separate device that is connected with the control unit 20 in a wireless manner.

Instead of four input elements as shown in FIG. 3, the user interface may have one, two, three, five, six or any number of input elements. In some embodiments, the light emission unit 10 is free of any user interface and may be arranged to operate in an automated manner. Other or additional functions than the functions as described above may be realized via the user interface.

FIG. 4A shows one example arrangement of a plurality of first and second LED dies 102 and 103 mounted on a substrate 100A. A plurality of first LED dies 102 has 57 members. A plurality of second LED dies 103 has seven members. The seven members of the second sub-plurality of second LED dies 103 are identified by their matrix positions as $103_{A1}$, $103_{E1}$, $103_{H1}$, $103_{A5}$, $103_{E5}$, $103_{A8}$, and $103_{H8}$. The plurality of first LED dies 102 is arranged to emit at a far red or infrared (IR) wavelength (first wavelength), which is essentially invisible to the human eye. The first LED dies are used for applying a treatment light pulse to a skin surface. The second LED dies 103 are arranged to emit in the visible wavelength range of between 400 nm and 700 nm, and the second LED dies may in particular be arranged as low radiant flux LED dies not suitable for emitting light at an intensity level sufficient for temporal hair removal (e.g. the second LED dies may have a specified forward current of below 100 mA, in particular of around 50 mA or 20 mA at around 2 V supply voltage). The second LED dies are used to emit a visible light pulse simultaneously with the invisible treatment light pulse. In addition, the second LED dies may be used to indicate an active area of the LED die matrix in particular in time periods outside of the duration of the treatment light pulse. Switched on second LED dies $103_{A1}$, $103_{E1}$, $103_{A5}$, and $103_{E5}$ then indicate that only the first LED dies arranged between those four second LED dies will be used for applying light to the skin (the first active area A1 is indicated by a dashed line), while switched on second LED dies $103_{A1}$, $103_{H1}$, $103_{A8}$, and $103_{H8}$ indicate that the full plurality of first LED dies will be used (the second active area A2 is indicated by a dashed-dotted line). The smaller first active area A1 may be useful for facial skin treatment (the smaller active area A1 allows more precisely targeting small facial regions), while the larger active area A2 may be useful for body skin treatment (faster treatment). As already mentioned above, an input element may be provided to allow a user to switch between the possible active areas. Depending on the pattern of the LED dies, at least two second LED dies may be used to indicate the active area (e.g. the second LED dies may be arranged in the opposite corners of a square or rectangular arrangement). In some embodiments, the active area of first LED dies may be surrounded by second LED dies to indicate the active area (e.g. in addition to emitting a visible light pulse). It is noted that instead of having second LED dies for indicating the active area of first LED dies, this function may be taken over by third LED dies and the at least one second LED die is disposed elsewhere.

Generally, in some embodiments, just a single second LED die is mounted on the substrate (e.g. a first sub-plurality of 63 first LED dies may be mounted on the substrate in an 8 times 8 matrix as shown in FIG. 4A and only one second LED die). The second LED is then arranged to emit light in the visible wavelength range (i.e. in between 400 nm and 700 nm) in particular at a low radiant flux (e.g. below 100 mW, typically with a forward current of around 20 mA to 50 mA). Such a second LED die is controlled to emit the visible light simultaneously with the emission of the treatment light pulse.

In some embodiments, two or three second LED dies are mounted on the substrate in close spatial relationship, where the two or three second LEDs each emit at a different visible wavelength (e.g. the wavelengths of the second LED dies may be chosen from the wavelength group comprising about 625 nm, about 520 nm, and about 465 nm—thus the three second LED dies essentially provide the functionality of an RGB LED) so that individual intensity control of the three second LED dies will allow to customize the overall light color that is emitted by the three second LED dies and it in particular allows the generation of a natural white color. This plurality of second LED dies may be used for illumination purposes or just for indicating visually that the otherwise not visible treatment light pulse is emitted onto the skin. An input element may be provided so that a user can set the favored color. Generally, the skin treatment device (and in particular a control unit) may be arranged to influence at least one of the intensity or color of the visible light emitted by the at least one second LED die (of course, the color can only be changed if at least two second LED dies are present that emit at different visible wavelengths). In particular, the intensity or color change may be used to indicate a battery charge state, to communicate a chosen skin treatment mode, to indicate a device temperature value, to communicate a chosen or applied radiant fluence value etc. E.g. red light may indicate that a battery of the skin treatment device is soon to be replaced or recharged, while a blue light may indicate that the skin treatment device is getting too hot and will soon inhibit further treatment light pulses.

FIG. 4B shows an example embodiment of an four times fifteen LED die matrix mounted on a substrate 100AA similar to the embodiment shown in FIG. 4A, where in addition to a plurality of 54 first LED dies 102A arranged for emitting treatment light pulses a plurality of six second LED dies 103A is arranged to emit light in the visible wavelength range in order to indicate a first active area A3 or a larger second active area A4. Such a rectangular LED die array may in particular be used in a skin treatment device that is continuously moved over the skin instead of subsequently moved from one skin treatment area to another skin treatment area, for which an LED die array as shown in FIG. 4A may be used. The gliding movement may occur in particular in a direction perpendicular to the long axis of the rectangular LED die array. In some embodiments, a glidingly utilized skin treatment device may comprise a speed sensor for determining the speed by which the device is moved across the skin. The skin treatment device may then be arranged to control the time period between consecutive treatment light pulses in dependence on the determined gliding speed, so that the treatment light pulses are seamlessly applied onto the skin (i.e. essentially without gaps or overlap). Due to the rectangular shape, the smaller active area A3 covers the full width of the LED matrix, which helps in a precise positioning of the small active area A3 onto the treatment area.

FIG. 5 shows an example embodiment of an 8 times 8 matrix of LED dies, where a plurality of thirty-two first LED dies 104 and a plurality of thirty-two second LED dies 105 are mounted on a substrate 100B in a checkerboard pattern (e.g. leading to an essentially homogeneous distribution of the first and of the second LED dies over the mounted substrate area). The plurality of second LED dies may be able to emit at a radiant flux that is alone also sufficient for at least temporal hair removal, but the second LED dies may also emit at a radiant flux that is sufficient for skin rejuvenation or other skin treatments. Then, the second LED dies (i.e. at least one of the second LED dies) are used to emit a visible light pulse simultaneously with the invisible treatment light pulse of the first LED dies, but the device may have a mode in which the plurality of second LED dies is also activated to emit a treatment light pulse (e.g. for acne treatment, where bluish light having a wavelength of about 410 nm can be used. Instead of being arranged in a checkerboard pattern, the first and second LED dies may also be arranged in any other pattern and there may be more or less second LED dies than first LED dies (e.g. two, seven, ten, sixteen, twenty, forty etc.). As had been mentioned before, the here depicted eight times eight matrix is just for illustration purposes and any arbitrary number of first and second LED dies may be arranged in any arbitrary pattern.

FIG. 6 shows another example embodiment of an 8 times 8 matrix of LED dies mounted on a substrate 100C, where three different sub-pluralities of first LED dies 106, 107, 108 are mounted on the substrate 100C and in addition two second LED dies 109 are mounted on the substrate as well. A first sub-plurality of twenty first LED dies 106, a second sub-plurality of twenty-one first LED dies 107, and a third plurality of twenty-one first LED dies 108 are mounted on the substrate in an alternating fashion. In the center of the LED die array two second LED dies 109 are mounted that are arranged to emit in the visible wavelength range at a radiant flux suitable for illumination purposes. In some embodiments, the first sub-plurality of first LED dies 106 may be arranged to emit at a first wavelength (e.g. at 850 nm), the second sub-plurality of first LED dies 107 may be arranged to emit at a second wavelength different to the first wavelength (e.g. 730 nm) and the third plurality of third LED dies 108 may be arranged to emit at a third wavelength (e.g. 505 nm) different to the first and second wavelength.

Figure 7A:
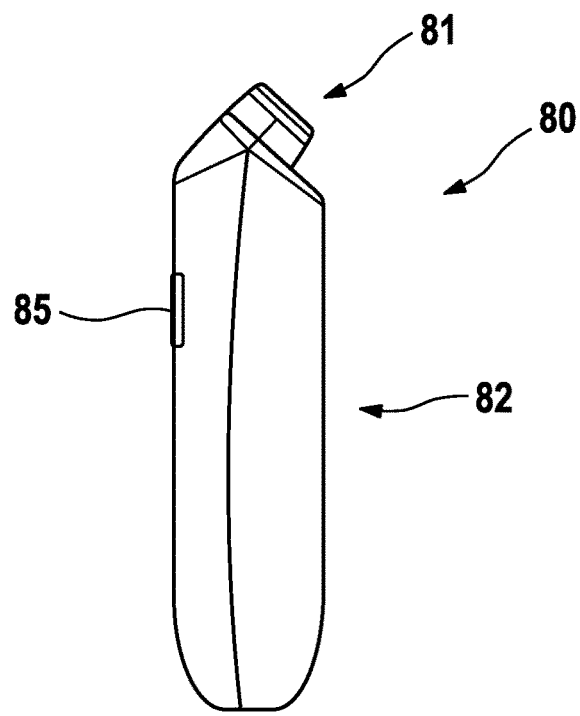
FIG. 7A is a side view of an example embodiment of a skin treatment device in accordance with the present disclosure.
Figures 7B, 7C, 7D:
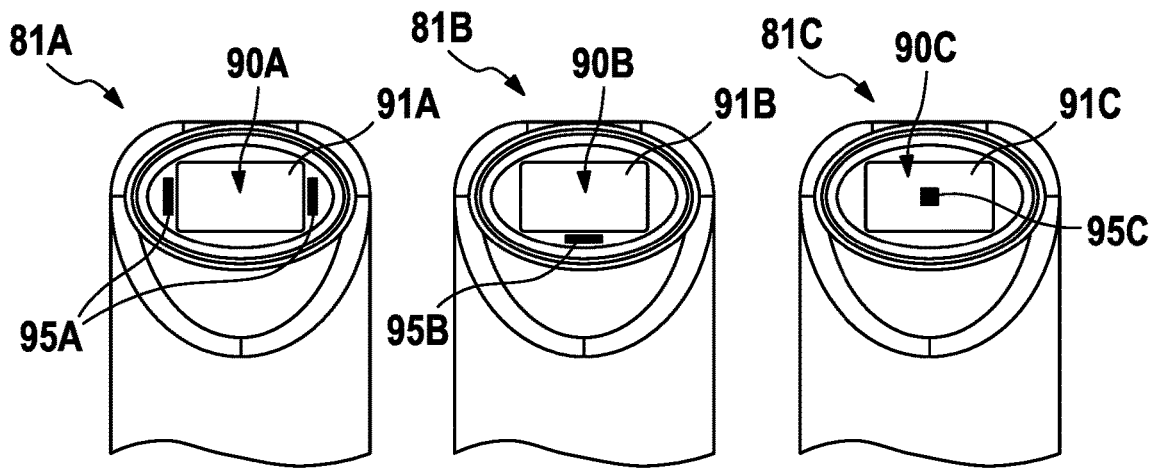
FIGS. 7B-D are front views onto various example heads of a skin treatment device as shown in FIG. 7A, where different positions of an additional sensor for measuring a skin property is indicated.

FIG. 7A shows a depiction of a skin treatment device 80 in accordance with the present invention. A light emission unit as described in the previous paragraphs is used in the skin treatment device 80. The skin treatment device 80 has a head section 81 for emission of treatment light pulses and a handle section 82 for holding of the skin treatment device 80 by a user's hand. A control element 85 is arranged at the handle section 82 for at least switching ON/OFF the skin treatment device 80. FIGS. 7B to 7D show front views of different embodiments of the head section 81A, 81B, 81C, where the embodiments differ essentially only in the location of a sensor or several sensors 95A, 95B, 95C for measuring at least one skin property. The head sections 81A, 81B, 81C each have a respective exit opening 90A, 90B, or 90C through which the treatment light pulses and the simultaneous visible light pulses will be emitted during operation (the exit opening is a common exit opening for the invisible and the visible pulse). A substrate with a plurality of LED dies mounted on the substrate may be arranged closely behind the exit opening 90A, 90B, 90C or the substrate may be arranged with a certain distance of about or less than 10 mm to the exit opening 90A, 90B, 90C inside of the head section 81A, 81B, 81C. An exit window 91A, 91B, 91C made from a material being essentially transparent to the light to be emitted by the LED dies covers the exit opening 90A, 90B, 90C. The exit opening 90A, 90B, 90C may have a size in the range of between 0.2 mm$^2$ to 10 cm$^2$, in particular in the range of 1 cm$^2$ to 4 cm$^2$. The mounted area of the substrate may then have the same size and shape as the exit opening 90A, 90B, 90C. In some embodiments, no exit window 91A, 91B, 91C is present. In the embodiment of FIG. 7B, the skin treatment device comprises two sensors 95A for measuring at least one skin property, which two sensors 95A are arranged on two opposite sides of the exit opening 90A. In the embodiments shown in FIGS. 7C and 7D, only a single sensor 95B and 95C, respectively, for measuring at least one skin property is arranged on the head section 81B and 81C, respectively. In FIG. 7C, the sensor 95B is arranged underneath the exit opening 90B, so that the sensor 95B is arranged before the exit opening 90B with respect to the usual movement direction (the device in accordance with FIG. 7C may be used in gliding mode). In FIG. 7D, the sensor 95C is arranged in a center area of the exit opening 90C. In such a case, the substrate disposed close to the exit opening 90C may have a respective cutout so that the sensor can be arranged in the cutout or can operate through the cutout. The sensor or sensors 95A, 95B, 95C may also allow determining skin contact, so that a control unit of the light emission unit may be arranged to only trigger the emission of a treatment light pulse in case a skin contact is determined.

Figure 8:
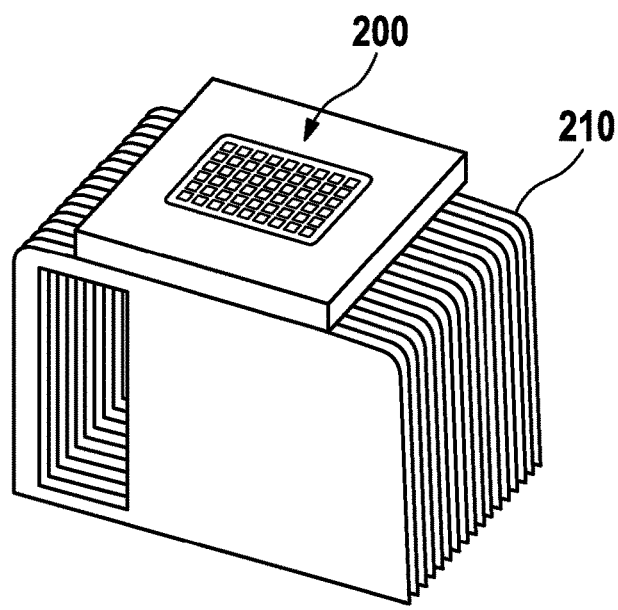
FIG. 8 is a schematic depiction of an array of LED dies mounted on a substrate, which substrate is in turn mounted on a heat sink to carry away excess heat.

FIG. 8 is a depiction of a substrate mounted LED die array 200 that is mounted on a heat sink 210 to convey away excess heat generated by the LED dies in operation. A fan may be arranged close to the heat sink to support the heat dissipation away from the heat sink.

Figure 9A:
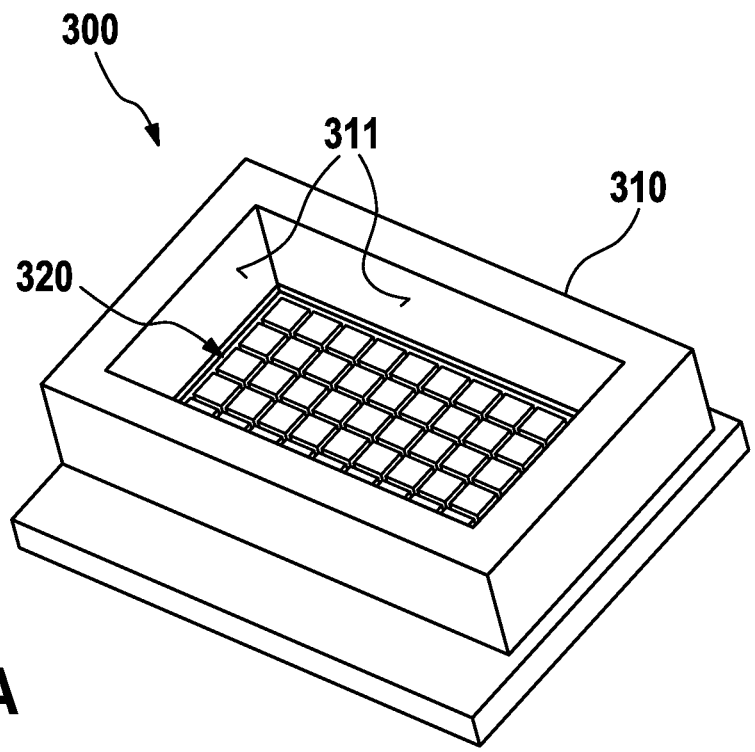
FIG. 9A is a depiction of an array of LED dies mounted on a substrate with a casing having inner reflective walls arranged around the mounted substrate area.
Figure 9B:
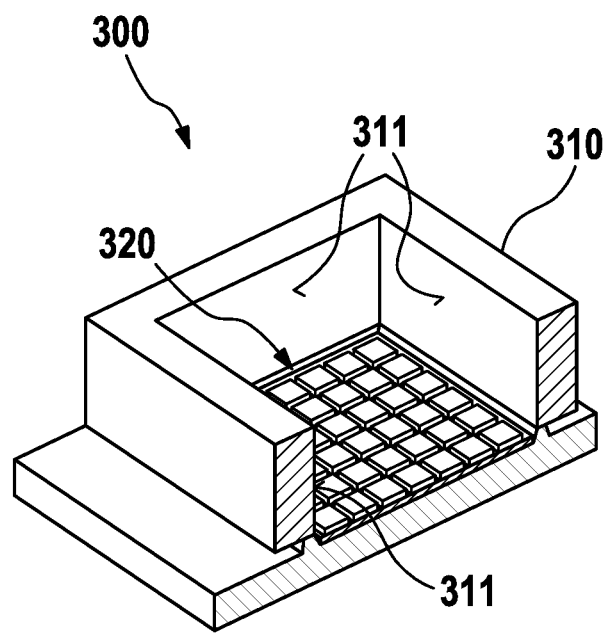
FIG. 9B is a cut-open depiction of the LED array with casing shown in FIG. 9A.

FIGS. 9A and 9B show a perspective view and a cut through a substrate mounted LED die array 300, where a casing 310 is mounted around the mounted area 320. The casing 310 has inner wall surfaces 311 that are highly reflective for the light that is emitted by the LED dies. The inner wall surfaces 311 may have a reflective coating, may be made from polished metal or from a diffusely reflecting plastic or ceramic material. The casing 310 then serves to guide the light emitted by the LED dies in an essentially loss-free manner from the LED die level to an exit opening of the skin treatment device and the radiant flux on the level of the LED dies is essentially the same as the radiant flux measured on the treatment area when the exit opening is placed on the skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin treatment device, in particular a temporal hair removal device, comprising:

a light emission unit comprising a substrate, a plurality of first LED dies mounted on the substrate on an area in the range of between about 0.2 cm$^2$ and about 100 cm$^2$, where the first LED dies are each arranged for emitting light at a first peak emission wavelength in the far red or infrared wavelength range of between about 700 nm and about 980 nm, and at least one second LED die arranged for emitting light at a second peak emission wavelength in the visible wavelength range of between about 400 nm and below about 700 nm;

wherein the skin treatment device is arranged to activate the first LED dies to emit a treatment light pulse and the first LED dies have a radiant flux such that a radiant fluence on the skin of a user in a range of between about 1 J/cm$^2$ and about 30 J/cm$^2$ is achieved by application of the treatment light pulse; and the skin treatment device is arranged to activate the at least one second LED die to emit a visible light pulse simultaneously with the emission of the treatment light pulse.

2. The skin treatment device in accordance with claim 1, wherein the treatment light pulse has a pulse length in the range of between about 10 ms and about 300 ms.

3. The skin treatment device in accordance with claim 1, wherein the first LED dies are mounted on the substrate on an area in the range of between about 1.0 cm$^2$ and about 10 cm$^2$.

4. The skin treatment device in accordance with claim 1, further comprising an exit opening and the skin treatment device is arranged so that the treatment light pulse and the visible light pulse exit the skin treatment device via the exit opening.

5. The skin treatment device in accordance with claim 4, wherein the control unit is arranged to activate the second LED die to emit visible light also outside of the duration of the treatment light pulse.

6. The skin treatment device in accordance with claim 1, further comprising a control unit for activating the first LED dies to emit the treatment light pulse and the at least one second LED die to emit the visible light pulse simultaneously with the treatment light pulse.

7. The skin treatment device in accordance with claim 1, wherein the first peak emission wavelength lies in a wavelength range of between about 700 nm and about 780 nm.

8. The skin treatment device in accordance with claim 1, wherein the first peak emission wavelength lies in a wavelength range of between about 800 nm and about 900 nm.

9. The skin treatment device in accordance with claim 1, wherein each of the first LED dies has a radiant flux in a range of between about 0.6 Watt and 10 Watt applicable over the pulse length.

10. The skin treatment device in accordance with claim 1, wherein the skin treatment device further comprises at least one sensor for measuring a skin property and a control unit coupled with the skin sensor for controlling the LED dies based on the skin property measured by the sensor.

11. The skin treatment device in accordance with claim 1, further comprising a control element for switching between a first skin treatment function and a second skin treatment function.

12. The skin treatment device in accordance with claim 1, comprising at least a further second LED die that is arranged for emitting light at a further peak emission wavelength in the visible range of between about 400 nm and about 700 nm, which further peak emission wavelength is different to the second peak emission wavelength.

13. The skin treatment device in accordance with claim 1, wherein the device is arranged to control at least one of the intensity or color of the visible light pulse.

14. The skin treatment device in accordance with claim 13, wherein the device controls the intensity of the color in dependence on at least one of a user's input, a chosen skin treatment function, a radiant fluence of the treatment light pulse, a battery charge status, or a device temperature value.

15. The skin treatment device in accordance with claim 1, further comprising a switch for user-controlled activation of the emission of a visible light pulse by the at least one second LED die.

16. The skin treatment device in accordance with claim 1, wherein the at least one second LED die is also mounted on the substrate.

17. The skin treatment device in accordance with claim 1, comprising at least three second LED dies mounted on the substrate, which second LED dies are disposed at locations suitable to indicate a selected active area of the first LED dies and the skin treatment device is arranged to have two selectable active areas of different size, where the larger selectable active area comprises the smaller selectable active area.

\* \* \* \* \*